US011225447B2

(12) United States Patent
George et al.

(10) Patent No.: US 11,225,447 B2
(45) Date of Patent: Jan. 18, 2022

(54) PROCESS FOR PURIFICATION OF OLEFIN FEED COMPRISING 1234YF

(71) Applicant: SRF LIMITED, Gurgaon (IN)

(72) Inventors: Jose George, Gurgaon (IN); Sunil Raj, Gurgaon (IN); Ambuj Kumar Mishra, Gurgaon (IN); Anurag Katiyar, Gurgaon (IT); Anurag Jain, Gurgaon (IN); Sudip Maity, Gurgaon (IN)

(*) Notice: Subject to any disclaimer, the term of this patent is extended or adjusted under 35 U.S.C. 154(b) by 0 days.

(21) Appl. No.: 17/054,863

(22) PCT Filed: May 13, 2019

(86) PCT No.: PCT/IN2019/050380
§ 371 (c)(1),
(2) Date: Nov. 12, 2020

(87) PCT Pub. No.: WO2019/220454
PCT Pub. Date: Nov. 21, 2019

(65) Prior Publication Data
US 2021/0214293 A1    Jul. 15, 2021

(30) Foreign Application Priority Data

May 16, 2018 (IN) .............................. 201811018315
May 16, 2018 (IN) .............................. 201811018316
(Continued)

(51) Int. Cl.
*C07C 17/383* (2006.01)
*C07C 17/389* (2006.01)
(Continued)

(52) U.S. Cl.
CPC ............ *C07C 17/386* (2013.01); *C07C 17/38* (2013.01); *C07C 17/383* (2013.01);
(Continued)

(58) Field of Classification Search
None
See application file for complete search history.

(56) References Cited

U.S. PATENT DOCUMENTS 2,931,840 A    4/1960  Marquis
9,302,964 B2   4/2016  Furuta et al.

FOREIGN PATENT DOCUMENTS

WO    2015053339 A1    4/2016
WO    2017108519 A1    6/2017
(Continued)

OTHER PUBLICATIONS

International publication WO2015053339A1, English translation, Apr. 16, 2015, pp. 1-14 (Year: 2015).*

*Primary Examiner* — Medhanit W Bahta
(74) *Attorney, Agent, or Firm* — Abelman, Frayne & Schwab; Stefan Knirr (57) ABSTRACT

The present invention relates to a process for purifying olefin feed comprising R-5 1234yf, R-40, R-134a, R-134, R-1225zc, and OFCB, comprising the step of separating different ternary and binary azeotrope compositions comprising 1234yf. The olefin feed is obtained from the pyrolysis of tetrafluoroethylene/chlorodifluoromethane with chloromethane/methane, optionally in presence of initiator.

10 Claims, 5 Drawing Sheets

(30) Foreign Application Priority Data

| | | |
|---|---|---|
| May 16, 2018 | (IN) | 201811018317 |
| Aug. 2, 2018 | (IN) | 201811004045 |
| Mar. 28, 2019 | (IN) | 201911012110 |

(51) Int. Cl.

| | |
|---|---|
| *C07C 17/38* | (2006.01) |
| *C07C 21/18* | (2006.01) |
| *C07C 19/08* | (2006.01) |
| *C07C 19/10* | (2006.01) |
| *C07C 17/386* | (2006.01) |
| *C07C 17/269* | (2006.01) |
| *C07C 17/275* | (2006.01) |
| *C07C 17/266* | (2006.01) |
| *C07C 17/278* | (2006.01) |

(52) U.S. Cl.
 CPC .......... *C07C 17/389* (2013.01); *C07C 17/266* (2013.01); *C07C 17/269* (2013.01); *C07C 17/275* (2013.01); *C07C 17/278* (2013.01)

(56) References Cited

FOREIGN PATENT DOCUMENTS

| | | |
|---|---|---|
| WO | 2017108522 A1 | 6/2017 |
| WO | 22017108524 A1 | 6/2017 |
| WO | 2017199999 A1 | 7/2017 |

\* cited by examiner

PROCESS FOR PURIFICATION OF OLEFIN FEED COMPRISING 1234YF

CROSS REFERENCE TO RELATED APPLICATIONS

This application is a national phase of PCT application No. PCT/IN2019/050380, filed May 13, 2019, which claims priority to IN patent application No. 201811004045, filed Aug. 2, 2018, IN patent application No. 201811018315, filed May 16, 2018, IN patent application No. 201811018316, filed May 16, 2018, IN patent application No. 201811018317, filed May 16, 2018, and IN patent application No. 201911012110, filed Mar. 28, 2018, all of which are incorporated herein by reference thereto.

FIELD OF THE INVENTION

The present invention relates to a process for purifying olefin feed comprising R-1234yf, R-40, R-134a, R-134, R-1225zc, and OFCB.

BACKGROUND OF THE INVENTION

Refrigerant is the substance which is used as working fluid in a thermodynamic cycle, undergoes a phase change from liquid to vapour and produces cooling. These are used in refrigeration, air conditioning, and heat pumping systems. They absorb heat from one area, such as an air conditioned space, and reject it into another, such as outdoors, usually through evaporation and condensation, respectively. These phase changes occur both in absorption and mechanical vapour compression refrigeration systems, but they do not occur in systems operating on a gas cycle using a fluid such as air. Fluorocarbon based fluids have found widespread use in industry in a number of applications, including as refrigerants, aerosol propellants, blowing agents, heat transfer media, and gaseous dielectrics. Tetrafluoropropenes, having zero ozone depletion and low global warming potential, have been identified as favorable refrigerant over other refrigerants. One tetrafluoropropene having valuable properties is 2,3,3,3-tetrafluoropropene (R-1234yf).

However, the production of these and other organofluorine compounds often require substantial separation steps to isolate the compounds from other components present in the reaction product, including unreacted feedstock, undesirable byproducts, and coproducts.

Production of organofluorine compounds often results in the formation of other organofluorine compounds, organochlorines, and chlorofluorocarbons (collectively referred to herein as 'coproducts of organofluorine production' or simply 'coproducts'), as both intermediate products and coproducts that appear in the final reaction mixture.

In prior art several methods have been disclosed for preparing R-1234yf, wherein by-products have been removed by using several techniques such as distillation, azeotropic distillation, adsorption, absorption, membrane separation and a like or combination thereof to achieve high yield.

U.S. Pat. No. 2,931,840 describes a reaction involving the pyrolysis of chloromethane with tetrafluoroethylene, or alternatively chloromethane with chlorodifluoromethane. It is very difficult to remove unreacted chloromethane and other side products from the reaction product stream. It does not mention the process for removing unreacted chloromethane and the side products from the reaction mixture.

U.S. Pat. No. 9,302,964 discloses a method for producing 2,3,3,3-tetrafluoropropene, the method comprising contacting an azeotropic composition or azeotrope-like composition of 2,3,3,3-tetrafluoropropene and chloromethane with an extraction solvent to obtain 2,3,3,3-tetrafluoropropene containing substantially no chloromethane.

PCT publication no. 2017/108519 discloses a process for purifying 2,3,3,3-tetrafluoro-1-propene (R-1234yf) from a first composition comprising 2,3,3,3-tetrafluoro-1-propene, 3,3,3-trifluoropropene (R-1243zf), trans-1, 3,3,3-tetrafluoro-1-propene (R-1234ze-E) and optionally or not at least one compound selected from the group consisting of chloromethane (R-40), 1,1-difluoroethane (R-152a), chloropentafluoroethane (R-115), 1,1,1,2-tetrafluoroethane (R-134a), trans-1,2,3,3,3-pentafluoropropene (R-1225ye-E); wherein the said process involves solvent extraction and extractive distillation methods.

PCT publication no. 2017/108522 discloses a process for purifying 2,3,3,3-tetrafluoro-1-propene (R-1234yf) from a first composition comprising 2,3,3,3-tetrafluoro-1-propene and chloromethane (R-40); wherein the said process involves solvent extraction and extractive distillation methods.

PCT publication no. 2017/108524 discloses a process for purifying 2,3,3,3-tetrafluoro-1-propene (R-1234yf) from a first composition comprising 2,3,3,3-tetrafluoro-1-propene, 1,1,1,2,2-pentafluoropropane (R-245cb) and trans-1,3,3,3-tetrafluoro-1-propene (R-1234ze-E); wherein the said process involves solvent extraction and extractive distillation methods.

Compounds having close boiling point to 2,3,3,3-tetrafluoropropene are 1,1,1,2-tetrafluoroethane (R-134a), 1,1,3,3,3-pentafluoropropene (1225zc), 1,1,2,2-tetrafluoroethane (R-134), chlorotrifluoroethene (CTFE) and chloromethane (R-40). Separation of these compounds by normal distillation is very difficult.

There is therefore a need to develop a process for purifying olefin feed by removing compounds having close boiling point to 2,3,3,3-tetrafluoropropene by mean of binary or ternary azeotrope or azeotrope like formation.

SUMMARY OF THE INVENTION

A first aspect of the present invention provides a process for purification of R-1234yf feed comprising R-1234yf, R-40, R-134a, R-134, R-1225zc, and OFCB, comprises a step of separating a ternary azeotrope composition "A" comprising R-1234yf, R-40 and R-134a.

An important embodiment of the first aspect of the present invention provides a process for purification of R-1234yf feed comprising R-1234yf, R-40, R-134a, R-134, R-1225zc, and OFCB, the process comprising the steps of:

a) passing the feed to a distillation column to separate top composition of ternary azeotrope containing R-1234yf, R-40 and R-134a;

b) optionally passing the ternary azeotrope composition "A" comprising R-1234yf, R-40 and R-134a through any one or more selected from an absorption tower, an adsorption tower and a semipermeable membrane;

c) passing the composition obtained from step b) to another distillation column to separate top composition of binary azeotrope composition "B" comprising R-1234yf and R-134a and bottom composition comprising substantially pure R-1234yf.

Another embodiment of present invention provides a process for purification of R-1234yf feed comprising R-1234yf, R-40, R-134a, R-134, R-1225zc, and OFCB, comprises a step of separating a binary azeotrope composition "B" comprising of 10 mole % to 35 mole % of R-134a and 60 mole % to 90 mole % of 1234yf.

A second aspect of the present invention provides a process for purification of R-1234yf feed comprising R-22, R-1234yf, R-40, R-134a, R-134, R-1225zc, and OFCB, comprising the steps of separating a top composition comprising R-22, OFCB, R-1234yf, R-40 and R-134a.

An embodiment of second aspect of the present invention provides a process for purification of R-1234yf feed comprising R-22, R-1234yf, R-40, R-134a, R-134, R-1225zc, and OFCB, the process comprising the steps of:
 a) passing the feed to a distillation column to separate top composition comprising R-22, OFCB, R-1234yf, R-40 and R-134a;
 b) passing the top composition comprising R-22, OFCB, R-1234yf, R-40 and R-134a through any one of more selected from an absorption tower, adsorption tower and semipermeable membrane;
 c) passing the composition obtained from step b) to another distillation column to separate top composition of binary azeotrope composition "B" comprising R-1234yf and R-134a and bottom composition comprising pure R-1234yf.

A third aspect of the present invention provides a process for purification of R-1234yf feed comprising R-1234yf, R-40, R-134a, R-134, R-1225zc, and OFCB, the process comprising the steps of:
 a) passing the feed through any one or more selected from an absorption tower, adsorption tower and semipermeable membrane;
 b) passing the composition obtained from step b) to another distillation column to separate top composition of ternary azeotrope composition "C" comprising R-1234yf, R-134, and R-134a and a bottom composition comprising substantially pure R-1234yf;
 c) recycling the top composition of ternary azeotrope composition "C".

An embodiment of third aspect of the present invention, provides a process for purification of R-1234yf feed comprising R-1234yf, R-40, R-134a, R-134, R-1225zc, and OFCB, the process comprising the steps of:
 a) passing the feed through any one or more selected from an absorption tower, adsorption tower and semipermeable membrane;
 b) passing the composition obtained from step b) to another distillation column to separate top composition of binary azeotrope composition "D" comprising R-1234yf and R-134 and a bottom composition comprising substantially pure R-1234yf;
 c) recycling the top composition of binary azeotrope composition "D".

An embodiment of third aspect of the present invention, provides a process for purification of R-1234yf feed comprising R-1234yf, R-134, the process comprising the steps of:
 a) passing the feed through any one or more selected from an absorption tower, adsorption tower and semipermeable membrane;
 b) passing the composition obtained from step b) to another distillation column to separate top composition of binary azeotrope composition "D" comprising R-1234yf and R-134 and a bottom composition comprising substantially pure R-1234yf;
 c) recycling the top composition of binary azeotrope composition "D".

A fourth aspect of the present invention provides a process for separating chlorocarbon from a feed comprising at least one fluoroolefinic and chlorocarbon by contacting the feed with a semipermeable membrane to obtain the feed substantially free of the chlorocarbon.

A fifth aspect of the present invention provides a process for preparing 1234yf, the process comprising the steps of:
 a) combining chlorodifluoromethane/tetrafluoroethylene and chloromethane/methane at a temperature to establish pyrolysis reaction to obtain a mixture 1;
 b) distilling the mixture 1 to vent out carbon monoxide to obtain mixture 2;
 c) distilling mixture 2 to vent out mixture 3 and obtain mixture 4;
 d) recycling the mixture 3;
 e) distilling mixture 4 to obtain 1234yf.

DETAILED DESCRIPTION

As used herein, the term 'azeotrope or azeotrope like' is intended in its broad sense to include both compositions that are strictly azeotropic and compositions that behave like azeotropic mixtures. An azeotropic mixture is a system of two or more components in which the liquid composition and vapor composition are equal at the stated pressure and temperature. In practice, this means that the components of an azeotropic mixture are constant boiling and cannot be separated during a phase change. As used herein, the term 'heavies' refers to a mixture comprising mainly of high boiling components having boiling points greater than R40 such as octafluorocyclobutane (OFCB), tetrafluorochloroethane, tetrafluoroethane, R-1224zc (3-chloro-1,1,3,3-tetrafluoropropene), R-1112 (2,2-dichloro-1,1-difluororoethene), R-236ca (1,1,2,2,3,3-Hexafluoropropane), R-236ea (1,1,1,2,3,3-Hexafluoropropane), R-1122 (2-chloro-1,1-difluoroethene), R-227ca (1,1,1,2,2,3,3-Heptafluoropropane), R-227ea (1,1,1,2,3,3,3-Heptafluoropropane), R-124 (2-chloro-1,1,1,2-tetrafluoroethane) which are recycled back to the reactor may be sent to incinerator. As used herein, the term 'lights' refers to component having boiling points lower than R1234yf such as R22 which are recycled back to the reactor.

As used herein, the term 'feed' used in the present invention refers to crude composition obtained by the reaction of tetrafluoroethylene/chlorodifluoromethane with chloromethane/methane, optionally in presence of initiator or catalyst known in the art.

As used herein, feed contains components selected from VdF (Vinylidenefluoride), tetrafluoroethene (TFE), R-32 (Difluoromethane), R-40 (chloromethane), R-1234yf (2,3,3,3-tetrafluoropropene), HFP (Hexafluoropropene), OFCB (octafluorocyclobutane), R-1225zc (1,1,3,3,3-pentafluoropropene), R-134a (1,1,1,2-tetrafluoroethane), R-134 (1,1,2,2-tetrafluoroethane), R-22 (Chlorodifluoromethane), CTFE (chlorotrifluoroethene), and heavies.

The feed can also be obtained by following the process disclosed in PCT publication PCT/IN2017/050006 and/or PCT publication PCT/IN2017/050555 filed by the same applicant.

The term "fluoroolefinic compounds" used in the present invention refers to unsaturated organofluorine compound. Examples of unsaturated organofluorine compounds includes R-1234yf, R-1234ze, R-1243zf, R-1233zd, R-1233xf, R-1225zc and mixtures thereof.

The term "chlorocarbon" used in the present invention refers to chlorinated hydrocarbons and chlorofluorocarbons (CFCs). Examples of CFCs includes CFC-11 ($CCl_3F$), CFC-12 ($CCl_2F_2$), HCFC-21 ($CHCl_2F$), HCFC-22 (R22; $CHClF_2$), HCFC-23 ($CHF_3$). Examples of chlorinated hydrocarbons includes chloromethane, methylene chloride, and carbon tetrachloride.

The selective permeability of a membrane is characterized by a separation factor α, which is a measure of the preferential permeability of one compound or type of compound over another compound or type of compound. The separation factor is the ratio of the relative amount of a compound that permeates through the membrane to the relative amount of another compound that permeates the membrane.

The Separation Factor $$\alpha=[A]\text{permeate}/[B]\text{permeate}[A]\text{retantate}/[B]\text{retentate}$$

The permeability is function of temperature, pressure and time.

The operable temperature ranges from 0° C. to 50° C. The operable pressure ranges from 1 bar to 10 bars The term "permeate" refers to the component of the feed that permeates through semipermeable membrane.

The term "retantate" refers to the component of the feed that does not permeates through semipermeable membrane.

The term "substantially free" used in the present invention refers to a composition that is 80% free of chlorocarbon compared to the feed.

The term "anhydrous" used in the present invention refers to water content of less than 50 ppm In an embodiment of the present invention, the feed is a non-azeotrope mixture obtained by passing the products obtained by the reaction of tetrafluoroethylene/chlorodifluoromethane and chloromethane/methane, through successive distillation columns.

In an embodiment of the present invention, the feed is a non-azeotrope mixture obtained by passing the product obtained by the reaction of tetrafluoroethylene/chlorodifluoromethane and chloromethane/methane, through three successive distillation columns, heat quencher, alkali scrubber, and/or sulfuric acid to remove moisture and/or alumina to remove moisture/acid to obtain a stream of gases free from moisture and acid.

Figure 1:
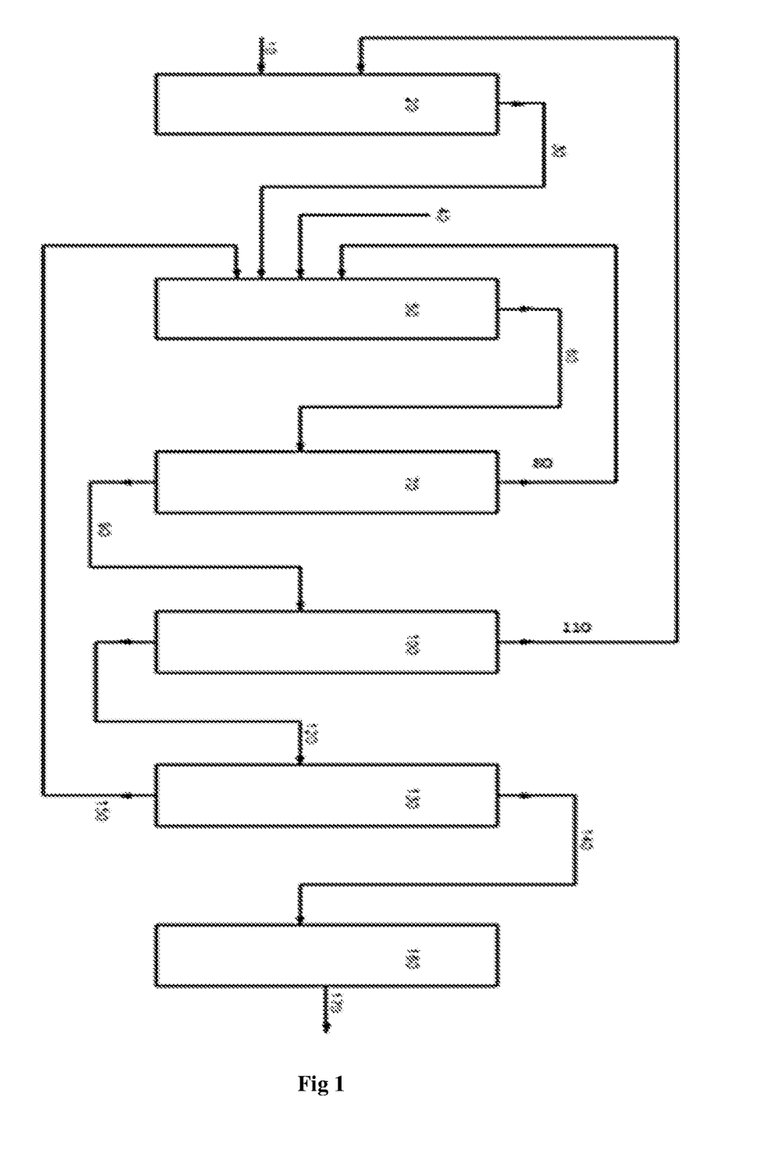
FIG. 1 illustrates the process for preparation of feed.

In another embodiment of the present invention, the feed is obtained from the process illustrated in FIG. 1. '10' of FIG. 1 represent chlorodifluoromethane being charged to the reactor '20' maintained at a temperature of about 700° C. to about 800° C. using an electric heater or steam. The stream of gases '30' mainly comprising tetrafluoroethene, along with '40' comprising of R-40 and an initiator such as carbon tetrachloride/hexachloroethane/trichloroacetylchloride/chloroform is fed to another reactor '50' maintained at a temperature of about 500° C. to about 800° C. using electrical heater or fired furnace. The stream '60' recovered from '50' is passed through quencher (heat quencher), alkali scrubber, sulfuric acid and alumina to obtain a stream of gases free of acid and moisture is fed to the distillation column '70'. '80', the lower boiling fractions recovered from '70' are fed back to the reactor '50', and the higher boiling fractions '90' comprising R-40, R-1234yf, HFP, OFCB, R-1225zc, R-134a, R-134, R-22, CTFE, and heavies are fed to the next distillation column '100'. '110', low boiling fraction comprising R-22 is fed to the reactor '20'. '120', the high boiling fraction comprising R-40, R-1234yf, OFCB, R-1225zc, R-134a, R-134, and heavies is fed to the next distillation column '130'. '140', the lower boiling fraction comprising R-1234yf, R-1225zc, R-134a, R-134, R-40, and OFCB is passed through absorption tower '160' to obtain feed '170'. '150', the higher boiling fractions comprising heavies is recycled back to the reactor '50'.

In another embodiment, the feed "170" may additionally contain R-22.

In another embodiment of the present invention, the feed is a non-azeotrope mixture obtained from the distillation column maintained at a temperature range of −29° C. to −23° C. at an atmospheric pressure.

In another embodiment of the present invention, the reaction of tetrafluoroethylene/chlorodifluoromethane with chloromethane/methane can be done in a batch reactor or semi-batch reactor or continuous reactor.

In a preferred embodiment of the present invention, the process of purification is performed in a continuous reactor.

In an embodiment of first and third aspects of the present invention, the feed comprises non-azeotrope mixture comprises of R-1234yf, R-40, R-134a, R-1225zc, R-134, and OFCB.

In an embodiment of first and third aspects of the present invention, the feed may contain heavies.

In an embodiment of first and third aspects of the present invention, the feed comprises non-azeotrope mixture comprises of about 20 mole % to about 35 mole % of R-1234yf, about 5 mole % to about 15 mole % of R-40, of about 0.5 mole % to about 20 mole % of R-134a, about 1 mole % to about 4 mole % of R-1225zc, about 1 mole % to about 4 mole % of R-134, about 20 mole % to about 45 mole % of OFCB and about 5 mole % to about 10 mole % of heavies and lights.

In an embodiment of the second aspect of the present invention, the feed comprises non-azeotrope mixture comprises of R-22, R-1234yf, R-40, R-134a, R-1225zc, R-134, OFCB and heavies.

In another embodiment of the second aspect of the present invention, R-22 may be added to the feed additionally before feeding it to the distillation column.

In another embodiment of the second aspect of the present invention, the feed may contain heavies.

In another embodiment of the second aspect of the present invention, the feed comprises non-azeotrope mixture comprises of about 5 mole % to about 25 mole % of R-22, of about 15 mole % to about 35 mole % of R-1234yf, about 20 mole % to about 45 mole % of R-40, of about 0.5 mole % to about 10 mole % of R-134a, about 0.1 mole % to about 10 mole % of R-1225zc, about 0.1 mole % to about 10 mole % of R-134, about 5 mole % to about 45 mole % of OFCB and about 3 mole % to about 5 mole % of heavies.

As used herein, the term absorption tower refers to the tower containing adsorption solvent selected from an alcohol, nitrile, chlorinated hydrocarbon, amides, ethers or esters.

In an embodiment of the present invention the absorption tower contains a solvent selected from a group consisting of dichloromethane, chloromethane, carbon tetrachloride, methanol, ethanol, isopropanol, diethyl ether, tetrahydrofuran, dioxane, acetonitrile, ethyl acetate, dimethylformamide, or the like.

In a preferred embodiment of the present invention the absorption tower contains chloroform or methanol.

In another embodiment of the present invention the adsorption tower contains molecular sieves having mean pore diameter of the size ranging from 3 Å to 12 Å.

In another embodiment of the present invention the adsorption tower contains molecular sieves having mean pore diameter of the size ranging from 3 Å to 5 Å.

As used herein, the term semipermeable membrane refers to polymeric membrane that allows selective permeability of one compound over the other in the feed. Examples of polymeric membrane include polyethene, polypropylene, polyester, polyamide, nylon, nitrile rubber, neoprene, polydimethylsiloxane (silicone rubber), chlorosulfonated polyethylene, polysilicone-carbonate copolymers, fluoroelastomer, polyvinylchloride, plasticized polyvinylchloride, polyurethane, cis-polybutadiene, cis-polyisoprene, poly(butene-1), polystyrene-butadiene copolymers, styrene/butadiene/styrene block copolymers, styrene/ethylene/butylene block copolymers, thermoplastic polyolefin elastomers, and block copolymers of polyethers and polyesters.

In another embodiment of the present invention, the semipermeable membrane includes polyethene or polypropylene.

As used herein, the ternary azeotrope composition "A" essentially contains R-1234yf, R-134a and R-40. The ternary azeotrope composition "A" may contain less than about 5 mole % of other components selected from the group consisting of R-134, R-22, R-1225zc and OFCB.

In an embodiment of the first aspect of the present invention, the ternary azeotrope composition "A" comprises about 52 mole % to about 62 mole % of R-1234yf, about 25 mole % to about 34 mole % of R-40 and about 2 mole % to about 25 mole % of R-134a.

In an embodiment of the first aspect of the present invention, the ternary azeotrope composition "A" comprises about 51.5 mole % of R-1234yf, about 30 mole % of R-40 and about 16 mole % of R-134a.

In an embodiment of the first aspect of the present invention, the ternary azeotrope composition "A" comprises about 51 mole % of R-1234yf, about 30 mole % of R-40 and about 15 mole % of R-134a.

In an embodiment of the first aspect of the present invention, the ternary azeotrope composition "A" comprises about 52.5 mole % of R-1234yf, about 27.2 mole % of R-40 and about 17.5 mole % of R-134a.

In an embodiment of the first aspect of the present invention, R-134a may be added to the distillation column to obtain the ternary azeotrope composition.

In another embodiment of the first aspect of the present invention, R-134a may be recovered through pressure swing distillation.

In an embodiment of the first aspect of the present invention, the mixture collected at the bottom of the distillation column after the separation of ternary composition, is recycled back to one of the initial distillation columns.

As used herein, the binary azeotrope composition "B" essentially contains R-1234yf and R-134a. The binary azeotrope composition "B" may contain less than about 5 mole % of other components selected from a group consisting of R-134, OFCB, R-1225zc and R-22.

In an embodiment of the present invention, the binary azeotrope composition "B" contains about 10 mole % to about 35 mole % of R-134a and about 60 mole % to about 90 mole % of 1234yf.

In another embodiment of the present invention, the binary azeotrope composition "B" is recycled back to the initial distillation columns.

Figure 2:
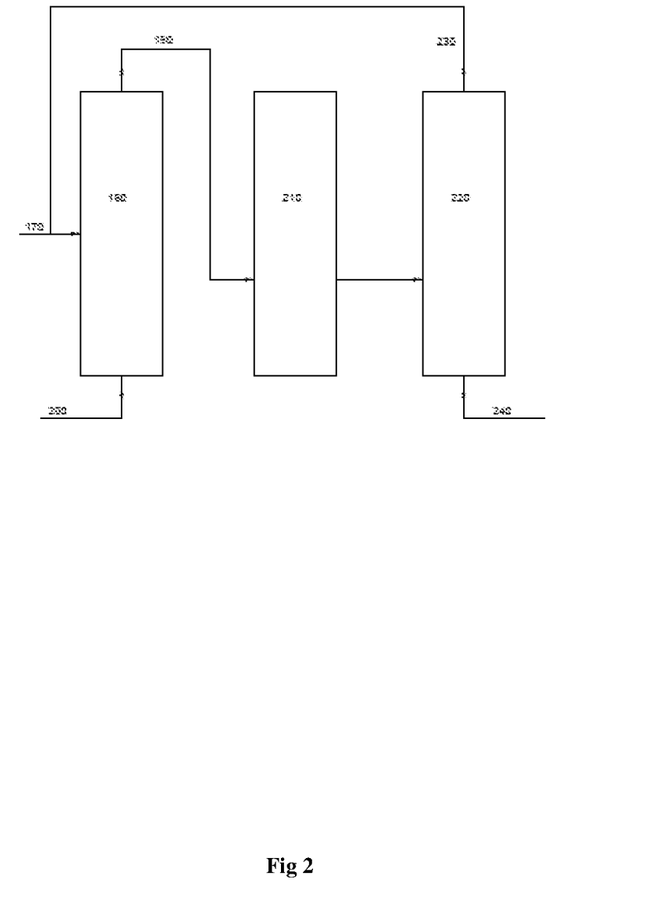
FIG. 2 illustrates first aspect of the present invention.

In another embodiment of the first aspect of the present invention, the process is as depicted in FIG. 2. As referred in FIG. 2, the feed '170' is fed to the distillation column '180' to recover R-22, which is fed back to the reactor, a low boiling fraction comprising a ternary azeotrope '190' and a high boiling fraction '200'. The ternary composition is fed to series of absorption tower, adsorption tower and semipermeable membranes '210'. The stream obtained through '210' is fed to another distillation column '220' to recover binary azeotrope composition '230', which is fed back to the distillation column '180' and '240' comprising substantially of 1234yf is recovered or optionally distilled.

In one embodiment of the second aspect of the present invention, the top composition comprises about 0.2 mole % to about 10 mole % of OFCB, about 1 mole % to about 10 mole % of R-134a, about 35 mole % to about 55 mole % of R-1234yf, about 12 mole % to about 40 mole % of R-22 and about 10 mole % to about 40 mole % of R-40.

In an embodiment of the second aspect of the present invention, the R-22 may be added to the feed before passing to the distillation column.

In another embodiment of the second aspect of the present invention, the top composition has less than 500 ppm of R-1225zc and R-134.

In another embodiment of the second aspect of the present invention, R-1225zc and R-134 are completely not detectable in the top composition.

It has been observed by the present inventors that R-22 improves separation of R-1234yf from R-1225zc and R-134 by increasing the relative volatility of R-1234yf.

Thus enabling 1234yf, R-40 and R-134a to boil along with R-22 without the close boiling components such as R-1225zc and R-134.

In the presence of R-22, ternary azeotrope of R-1234yf, R40 and R-134a comes along with binary azeotrope of OFCB and R40 which leads to the suppression of close boiling components like R-1225zc and R-134.

Figure 3:
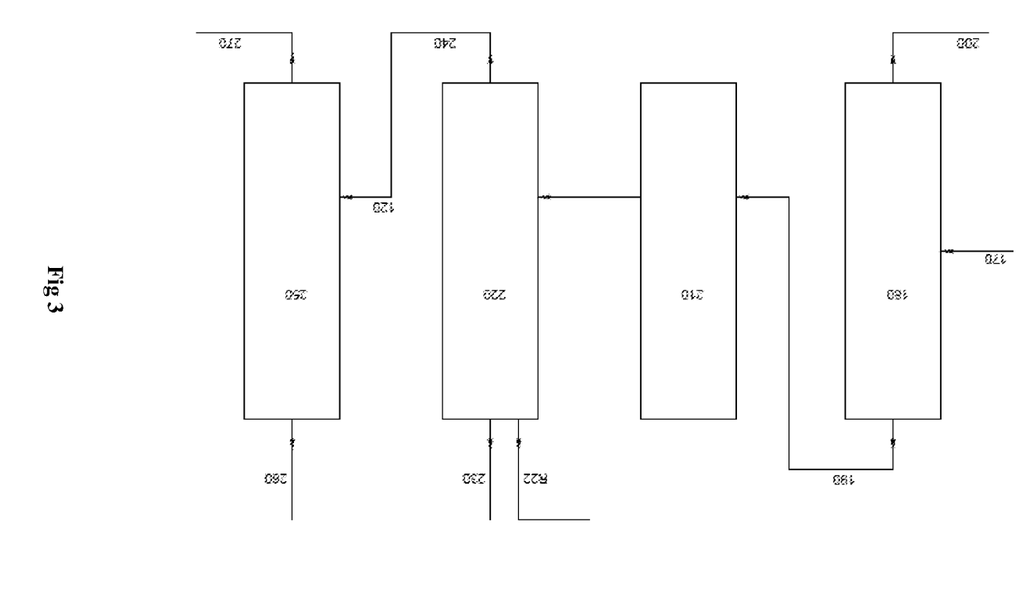
FIG. 3 illustrates second aspect of the present invention.

In another embodiment of the second aspect of the present invention, the process is as depicted in FIG. 3. As referred in FIG. 3, the feed "170" is fed to the distillation column "180" to recover a low boiling fraction "190", comprising R-22, R-1234yf, R-40, R-134a and OFCB and a high boiling fraction "200". The low boiling composition is fed to series of absorption tower, adsorption tower and semipermeable membranes "210". The stream obtained through "210" is fed to another distillation column "220" to recover R-22, the binary azeotrope composition "230" and "240" a high boiling fraction at the bottom of the column. The recovered R-22 is either sent back to the reactor "20" or to the distillation column "180". "240" is fed to the distillation column "250" to get a binary azeotrope composition "260" that is fed back to the distillation column "180" and "270" comprising substantially of 1234yf is recovered or optionally distilled.

In another embodiment of second aspect of the present invention, the mixture collected at the bottom of the distillation column after the separation of top composition, is recycled back to one of the initial distillation columns.

As used herein, the ternary azeotrope composition "C" of the third aspect of the present invention essentially contains R-1234yf, R-134a and R-134. The ternary azeotrope composition of the third aspect of the present invention may contain less than about 5 mole % of other components selected from a group consisting of OFCB and 1225zc.

In another embodiment of the third aspect of the present invention, R-134 is added to the distillation column to obtain the ternary azeotrope composition "C".

In another embodiment of the third aspect of the present invention, the ternary azeotrope composition "C" comprises of about 70 mole % to about 85 mole % of R-1234yf, about 5 mole % to about 15 mole % of R-134 and about 2 mole % to about 20 mole % of R-134a.

In another embodiment of the third aspect of the present invention, the ternary azeotrope composition "C", is recycled back to one of the initial distillation columns and the composition at the bottom of the distillation tower contains substantially pure R-1234yf.

In another embodiment of the third aspect of the present invention, the composition collected at the bottom of the distillation after the separation of ternary azeotrope composition "C" is sent for final distillation to get R-1234yf of purity more than 99%.

In another embodiment of the third aspect of the present invention, the feed after sequential treatment through adsorption tower, absorption tower and semipermeable membrane, gets distilled out as a binary azeotrope composition "D" essentially containing R-1234yf and R-134.

As used herein, the binary azeotrope composition "D" essentially contains R-1234yf and R-134. The binary azeotrope composition "D" may contain less than about 5 mole % of other components.

In an embodiment of the present invention, the binary azeotrope composition "D" comprises about 5 mole % to about 15 mole % of R-134 and about 85 mole % to about 95 mole % of 1234yf.

In an embodiment of the present invention, the binary azeotrope composition "D" comprises about 5 mole % to about 20 mole % of R-134 and about 80 mole % to about 95 mole % of 1234yf.

In another embodiment of the present invention, the binary azeotrope is recycled back to the initial distillation columns.

Figure 4:
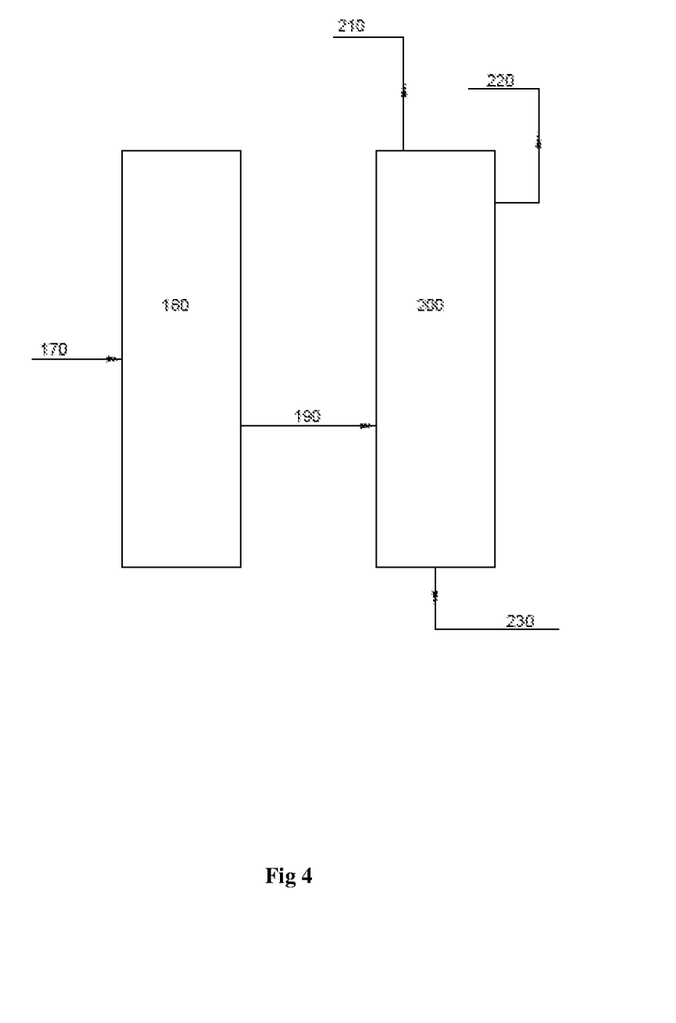
FIG. 4 illustrates third aspect of the present invention.

In another embodiment of the third aspect of the present invention, the process is as depicted in FIG. 4. As referred in FIG. 4, the feed '170' is fed to a series of absorption tower, adsorption towers or semipermeable membranes '180' to recover '190', comprising of R-134, R-1225zc, R-1234yf, R-134a and OFCB and high boiling fractions. The stream of '190' is fed to a distillation column to recover the ternary azeotrope composition '220' comprising R-1234yf, R-134a and R-134 or R-1234yf and R-134, and '230' comprising substantially of 1234yf. '220' is fed to the distillation column '180' and '230' comprising substantially of 1234yf is recovered or optionally distilled.

In an embodiment of fourth aspect, the present invention provides a process for separating chlorinated hydrocarbon from a composition comprising at least one fluoroolefinic compound by contacting the feed with a semipermeable membrane.

In another embodiment of fourth aspect, the present invention provides a process for separating chlorinated hydrocarbon from a composition comprising at least one R-1234yf and/or R-1234ze/R-1225zc/R-1233zd/R-1243zf by contacting the feed with a semipermeable membrane.

In another embodiment of fourth aspect, the present invention provides a process for separating chloromethane from a composition comprising at least one R-1234yf and/or R-1234ze by contacting the feed with a semipermeable membrane.

In another embodiment of fourth aspect, the present invention provides a process for separating chloromethane from a composition comprising R-1234yf by contacting the feed with a semipermeable membrane.

In an embodiment of fourth aspect, the present invention provides a process for separating chloromethane through semipermeable membrane, further recovering chloromethane and reusing recovered chloromethane for preparation of R-1234yf.

In an embodiment of fourth aspect, the present invention provides a continuous process for separating, recovering and reusing chloromethane comprising the step of contacting a feed containing at least one R-1234yf and/or R-1234ze with a semipermeable membrane.

In another embodiment of fourth aspect, the present invention provides a process for separating chloromethane (R-40) from a feed comprising R-1234yf, vinyledenefluoride, R-124a, HFP, OFCB, R-22, R-1122, R-236ca, R-226cb, R-32, TFE, trans R-1225ye, cis R-1225ye, R-1243zf, R-1234ze and R-40 by contacting the feed with a semipermeable membrane.

In another embodiment of fourth aspect of the present invention provides a process for separating chlorocarbon from a feed comprising at least one fluoroolefinic and chlorocarbon by contacting the feed with a semipermeable membrane to obtain a retantate substantially free of the chlorocarbon.

In another embodiment of fourth aspect, the present invention provides a process for separating chlorinated hydrocarbon from a feed comprising at least one fluoroolefinic compound by contacting the feed with a semipermeable membrane to obtain a retantate substantially free of the chlorocarbon.

In another embodiment of fourth aspect, the present invention provides a process for separating chlorinated hydrocarbon from a feed comprising at least one R-1234yf and/or R-1234ze/R-1225zc/R-1233zd/R-1243zf by contacting the said composition with a semipermeable membrane to obtain a retantate substantially free of the chlorocarbon.

In another embodiment of fourth aspect, the present invention provides a process for separating chloromethane from a composition comprising R-1234yf by contacting the feed with a semipermeable membrane to obtain a retantate substantially free of the chlorocarbon.

In another embodiment of fourth aspect, the present invention provides a process for separating chloromethane from a composition comprising R-1234yf by contacting the feed with a semipermeable membrane to obtain a retantate having not more than 10% of chlorocarbon compared to the feed.

In another embodiment of fourth aspect, the present invention provides a process for separating chloromethane from a composition comprising R-1234yf by contacting the feed with a semipermeable membrane to obtain a retantate having not more than 5% of chloromethane compared to the feed.

In another embodiment of fourth aspect, the present invention provides a process for separating chloromethane from a composition comprising R-1234yf by contacting the feed with a semipermeable membrane to obtain a retantate having not more than 2% of chlorocarbon compared to the feed.

In another embodiment of fourth aspect, the present invention provides a process for separating chloromethane from a composition comprising R-1234yf by contacting the feed with a semipermeable membrane to obtain a retantate having not more than 0.5%, of chloromethane compared to the feed.

In another embodiment of fourth aspect, the present invention provides a process for separating chloromethane (R-40) from a feed comprising R-1234yf, VdF, R-124a, HFP, OFCB, R-22, R-1122, R-236ca, R-226cb, R-32, TFE, trans R-1225ye, cis R-1225ye, R-1243zf, R-1234ze and R-40 by contacting the feed with a semipermeable membrane to obtain a retantate substantially free of R-40.

In another embodiment of fourth aspect, the present invention provides a process of using the retantate for preparing single fluoroolefinic compound.

In another embodiment of fourth aspect, the present invention provides a process of using the retantate for preparing R1234yf.

In an embodiment of fifth aspect of the present invention, the "mixture 1" comprises 1234yf, unreacted tetrafluoroethylene, chloromethane, chlorodifluoromethane and carbon monoxide.

In another embodiment of fifth aspect of the present invention, the "mixture 2" comprises 1234yf, unreacted tetrafluoroethylene, chloromethane, and chlorodifluoromethane.

In another embodiment of fifth aspect of the present invention, the "mixture 3" comprises unreacted tetrafluoroethylene, chloromethane, and chlorodifluoromethane.

In another embodiment of fifth aspect of the present invention, the "mixture 4" comprises 1234yf.

In another embodiment of fifth aspect of the present invention, the mixture 2 is substantially free from carbon monoxide.

In another embodiment of fifth aspect of the present invention, the mixture 3 comprising unreacted tetrafluoroethylene, chloromethane, and chlorodifluoromethane is recycled back to the pyrolysis reactor.

In another embodiment of fifth aspect of the present invention, the mixture 4 is passed through three successive distillation columns to obtain pure 1234yf.

Figure 5:
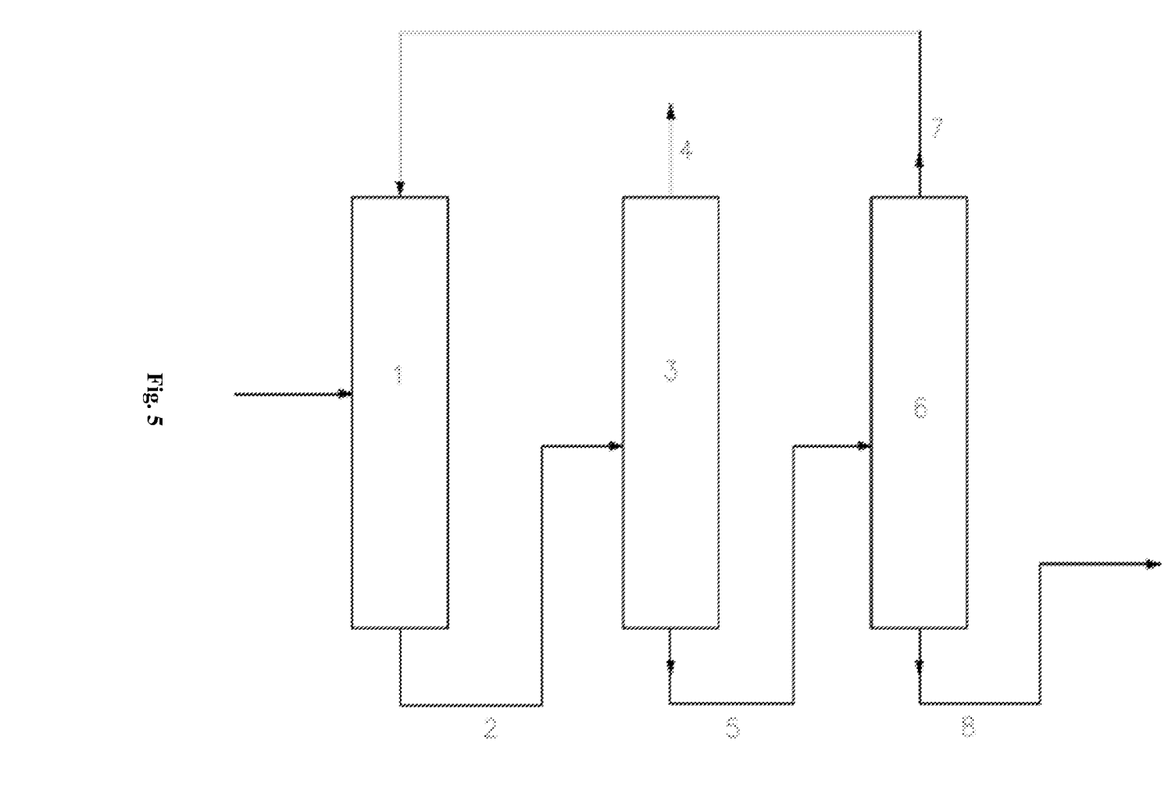
FIG. 5 illustrates fourth aspect of the present invention.

In another embodiment of fifth aspect of the present invention, the distillation od performed as illustrated in FIG. 5. Chlorodifluoromethane is charged to the reactor maintained at a temperature of about 700° C. to about 800° C. The stream of gases mainly comprising tetrafluoroethylene, along with R-40 and an initiator is fed to another reactor "1" maintained at a temperature of about 500° C. to about 750° C. The stream passed through quencher (heat quencher), alkali scrubber, sulfuric acid and alumina to obtain a stream of gases free of acid and moisture to obtain feed "2" comprising carbon monoxide, tetrafluoroethylene, HFP, OFCB, R-1225zc, R-134a, R-134, R-22, CTFE, R-236ca, R-236ca, R-1122, heavies and is fed to the distillation column '3'. '4', comprising carbon monoxide is vented out from the distillation column and heavier boiling fraction "5" comprising mixture 2 is fed to another column "6" to distill and recycle "7" comprising tetrafluoroethylene, the heavies "8" comprising 1234yf are passed through successive distillation columns to obtain 1234yf of high purity.

The present invention has been described in terms of its specific embodiments, certain modifications and equivalents will be apparent to those skilled in the art and are intended to be included within the scope of the present invention.

The following examples are given by way of illustration and therefore should not be construed to limit the scope of the present invention.

EXAMPLES

Example 1

Process for Purifying 1234yf Through Formation of Ternary Azeotrope Composition "A" and Binary Azeotrope Composition "B"

Tetrafluoroethene and chloromethane was reacted in the presence of initiator at a temperature range of 500-750° C. Low boiling fractions were removed from the resulting reactor outlet stream. The reactor outlet feed after removal of low boiling fraction and heavies have the following composition was transferred into distillation column.

Distillation Step 1:

Table 1 shows the composition of the feed sent to the distillation column.

TABLE 1

| Component of reactor outlet stream (after removal of lights) | Composition (Percentage by weight) |
| --- | --- |
| OFCB | 36.6 |
| R-134a* | 0.9 |
| R-1225zc | 1.8 |
| R-1234yf | 27.6 |
| R-134 | 1.5 |
| R-40 | 10.1 |
| Low boiling fractions | 7.0 |
| Heavies | 14.0 |

*134a was added to the above feed

Table 2 shows the composition of the different fractions in the distillation column 1.

TABLE 2

| Component of reactor outlet stream (after removal of lights) | Top Cut composition (Percentage by weight) | Bottom Cut composition (Percentage by weight) |
| --- | --- | --- |
| OFCB | Not detected | 56.09% |
| R-134a | 17.5% | 0.29% |
| R-227ea | Not detected | 1.31% |
| R-227ca | Not detected | 2.14% |
| R-1225zc | Not detected | 2.66% |
| R-1234yf | 52.5% | 15.03% |
| R-134 | Not detected | 1.87% |
| R-40 | 27.2% | 1.22% |
| Lights | 2.35% | Not detected |
| Heavies | Not detected | 19.39% |

It is clear from the Table 2 that the separation of ternary azeotrope suppresses contamination like 1225zc and 134.

A ternary azeotropic or azeotrope-like composition comprising R-1234yf: 52.5 mol %; R-134a: 17.5 mol % and R-40: 27.2 mol % is sent to the absorption, adsorption tower, semipermeable membrane and the next distillation tower.

Distillation Step 2:

Table 3 shows the composition of the different fractions in the distillation column 2.

TABLE 3

| Component of reactor outlet stream (after removal of lights) | Top Cut composition (Percentage by weight) |
| --- | --- |
| OFCB | Not detected |
| R-134a | 10-35 |
| R-1225zc | Not detected |
| R-1234yf | 60-89 |
| R-134 | 0-8 |

The top composition is sent back to the distillation column 1 and bottom composition contains R-1234yf of more than 99% purity.

Example 2

Process for Purifying 1234yf Through Formation of Top Composition Using R-22

Tetrafluoroethene and chloromethane was reacted in the presence of initiator at a temperature range of 500-750° C.

Low boiling fractions were removed from the resulting reactor outlet stream. The reactor outlet feed have the following composition was transferred into distillation column.

The reactor outlet stream comprising 10 to 15% R-22 is transferred into a distillation column. Presence of R-22 improves separation of R-1234yf from R-1225zc and R-134 by increasing the relative volatility as R-1234yf, R40 and R-134a comes along with R-22 without close boiling compounds like R-1225zc, R-134 etc.

Example 2a

Distillation Step 1:

TABLE 4

| Components | Top Cut composition (Percentage by mole) | Bottom Cut composition (Percentage by mole) |
| --- | --- | --- |
| OFCB | 0.36 | 66.04 |
| R-134a | 2.18 | 0.021 |
| R-1225zc | Not detected | 4.78 |
| R-1234yf | 41.14 | 2.49 |
| R-134 | Not detected | 3.66 |
| R-22 | 37.42 | 0.18 |
| R-40 | 16.79 | 11.31 |

Example 2b

TABLE 5

| Components | Top Cut composition (Percentage by weight) | Bottom Cut composition (Percentage by weight) |
| --- | --- | --- |
| OFCB | 13.28 | 6.85 |
| R-134a | 1.19 | 0.0 |
| R-1225zc | 0.01 | 1.10 |
| R-1234yf | 31.35 | 0.18 |
| R-134 | 0.01 | 1.55 |
| R-22 | 16.58 | 0.14 |
| R-40 | 36.68 | 22.45 |
| Heavies | 0.00 | 67.73 |

The results depicted in Tables 4 and 5 clearly indicates that impurities like R-1225zc and R-134 can be completely eliminated from the top composition. The product from the distillation column is then sent to a series of absorption, semipermeable membrane and adsorption tower. The product stream is then passed to a series of distillation column to remove R22, and the binary azeotrope containing R-134a and R-1234yf. The top composition is sent back to the distillation column 1 and bottom composition is distilled to get R-1234yf of more than 99% purity.

Example 3

Process for Purifying 1234yf Through Formation of Ternary Azeotrope Composition "C" and Binary Composition "D"

Tetrafluoroethene and chloromethane was reacted in the presence of intiator at a temperature range of 500-750° C. Low boiling fractions were removed from the resulting reactor outlet stream. The reactor outlet stream after removal of low boiling fraction and heavies have the following composition was transferred into distillation column.

Distillation Step 1:

Example 3a

The reactor outlet composition after removal of low boiling components is passed through a series of absorption column followed by adsorption column. The product stream is then passed through a distillation column from where R-134a, R-1234yf and R-134 is recovered from the top and bottom containing majority of R-1234yf is transferred to another distillation column from where pure R-1234yf is recovered.

The composition at the top of the second column from where R-134a, R-1234yf and R-134 is removed was R-134a: 4.0; R-1234yf: 83% and R-134:13%

Example 3b

The product stream is then passed through a distillation column from where R-1234yf and R-134 is recovered from the top and bottom containing majority of R-1234yf is transferred to another distillation column from where pure R-1234yf is recovered. A binary azeotrope of R-134 and R-1234yf is formed having a composition of 80-98% 2,3,3,3-tetrafluoropropene and 2-20% 1,1,2,2-tetrafluoroethane The top composition is sent back to the distillation column 1 and bottom composition is distilled at a pressure of atmospheric to 15 bar to get R-1234yf of more than 99% purity.

Example 4

The experiments were performed to show that the permeation of chloromethane from the feed is a function of temperature, pressure and time. Table 1 and Table 2 shows the results of permeation of chloromethane at 25° C. and a pressure of 1.1 bars. In this experiment, feed was allowed to pass through polyethene and analyzed over a period of time.

TABLE 6

| | Time (hours) | | | | | |
| --- | --- | --- | --- | --- | --- | --- |
| | 0 | 4.25 | 9 | 13.5 | 17.5 | 46 |
| Gas Weight | 57 | 55 | 55 | 55 | 55 | 26 |
| R-1234yf | 21.73% | 23.30% | 25.11% | 26.65% | 28.23% | 35.52% |
| R22 | 19.27% | 20.27% | 21.23% | 22.04% | 22.69% | 20.16% |
| R-40 (C-1) | 33.40% | 29.15% | 24.26% | 20.03% | 15.92% | 0.58% |

TABLE 7

| | Time hours | | | | | |
| --- | --- | --- | --- | --- | --- | --- |
| | 0 | 4.25 | 9 | 13.5 | 17.5 | 46 |
| Gas Weight | 51 | 49 | 49 | 49 | 49 | 29 |
| R-1234yf | 15.07% | 16.34% | 17.90% | 18.91% | 19.91% | 25.24% |
| R-22 | 31.10% | 32.74% | 34.60% | 35.89% | 36.80% | 36.00% |
| R-40 (C-1) | 30.42% | 25.69% | 20.38% | 16.51% | 13.16% | 1.20% |

Example 5

Comparative Example 5a: Tetrafluoroethene and chloromethane was reacted in the presence of carbon monoxide at a reaction temperature of 650° C.-700° C. Table 8 shows the composition of the furnace (reactor) inlet and outlet data when the pyrolysis is carried out in presence of carbon monoxide.

TABLE 8

|  | Reactor inlet | Reactor Outlet |
| --- | --- | --- |
| CO | 8.237% | 10.969% |
| CH4 | 0.097% | 0.088% |
| R-116 | 0.031% | 0.000% |
| TFE | 19.260% | 3.177% |
| R23 | 12.705% | 14.783% |
| VDF | 7.683% | 10.141% |
| R-32 | 0.736% | 1.037% |
| HFP | 0.009% | 0.652% |
| TriFethene | 0.000% | 0.239% |
| OFCB | 1.513% | 2.448% |
| 2,3,3,3-tetrafluoropropene | 0.000% | 4.917% |
| R-40 | 20.39% | 11.40% |
| Heavies | 29.34% | 36.45% |
| TFE Conversion | 84% | |
| 2,3,3,3-tetrafluoropropene Selectivity | 31% | |

Comparative Example 5b: Tetrafluoroethene and chloromethane was reacted in the presence of carbon monoxide at a reaction temperature of 650° C.-700° C.

Table 2 also shows the composition of the furnace (reactor) inlet and outlet data when the pyrolysis is carried out in presence of carbon monoxide.

TABLE 9

|  | Reactor inlet | Reactor Outlet |
| --- | --- | --- |
| CO | 9.018% | 10.907% |
| CH4 | 0.121% | 0.081% |
| R-116 | 0.038% | 0.000% |
| TFE | 16.915% | 3.086% |
| R23 | 14.028% | 15.928% |
| VDF | 8.524% | 10.315% |
| R-32 | 0.471% | 0.813% |
| HFP | 0.102% | 0.562% |
| TriFethene | 0.000% | 0.195% |
| OFCB | 1.202% | 1.811% |
| 2,3,3,3-tetrafluoropropene | 0.000% | 4.718% |
| R-40 | 20.21% | 12.78% |
| Heavies | 27.92% | 33.65% |
| TFE Conversion | 82% | |
| 2,3,3,3-tetrafluoropropene Selectivity | 34% | |

The comparative examples clearly indicate that when pyrolysis is carried out in presence of carbon monoxide, the formation of 2,3,3,3 tetrafluoropropene is less than 5%, conversion of TFE is less than 85% and selectivity towards 2,3,3,3-tetrafluoropropene is below 35%.

Example 5c

Tetrafluoroethene and chloromethane was reacted in the absence of carbon monoxide at a reaction temperature of 650° C.-700° C. Table 10 shows the composition of the furnace (reactor) inlet and outlet data when the pyrolysis is carried out in absence of carbon monoxide.

|  | Reactor inlet | Reactor Outlet |
| --- | --- | --- |
| CO | 0.130% | 0.190% |
| CH4 | 0.014% | 0.063% |
| R-116 | 0.025% | 0.000% |
| TFE | 23.271% | 1.813% |
| R23 | 5.909% | 9.751% |
| VDF | 5.256% | 10.859% |
| R-32 | 1.724% | 2.984% |
| HFP | 0.056% | 1.548% |
| TriFethene | 0.000% | 0.623% |
| OFCB | 0.781% | 2.477% |
| 2,3,3,3-tetrafluoropropene | 0.000% | 9.090% |
| C1 | 26.22% | 5.17% |
| Heavies | 34.91% | 40.21% |
| TFE Conversion | 92% | |
| 2,3,3,3-tetrafluoropropene Selectivity | 42% | |

Example 5d

Tetrafluoroethene and chloromethane was reacted in the absence of carbon monoxide at a reaction temperature of 650° C.-700° C. Table 11 shows the composition of the furnace (reactor) inlet and outlet data when the pyrolysis is carried out in absence of carbon monoxide.

|  | Reactor inlet | Reactor Outlet |
| --- | --- | --- |
| CO | 0.945% | 0.451% |
| CH4 | 0.157% | 0.048% |
| R-116 | 0.000% | 0.000% |
| TFE | 21.408% | 2.154% |
| R23 | 3.691% | 6.676% |
| VDF | 3.159% | 8.526% |
| R-32 | 4.024% | 3.889% |
| HFP | 0.723% | 2.215% |
| TriFethene | 2.428% | 1.459% |
| OFCB | 3.394% | 4.658% |
| 2,3,3,3-tetrafluoropropene | 0.000% | 10.210% |
| C1 | 24.77% | 4.92% |
| Heavies | 32.69% | 40.71% |
| TFE Conversion | 90% | |
| 2,3,3,3-tetrafluoropropene Selectivity | 53% | |

The experimental data obtained in examples 5c and 5d clearly indicate the advantage of CO removal on the conversion of TFE and on selectivity of 2,3,3,3-tetrafluoropropene.

The invention claimed is:

1. A process for purification of 2,3,3,3-tetrafluoro-1-propene (R-1234yf) feed comprising R-1234yf, chloromethane (R-40), 1,1,1,2-tetrafluoroethane (R-134a), 1,1,2,2-tetrafluoroethane (R-134), 1,1,3,3,3-pentafluoropropene (R-1225zc), and octafluorocyclobutane (OFCB), said process comprising a step of separating a ternary azeotrope composition "A" comprising about 52 mole % to about 62 mole % of R-1234yf, about 25 mole % to about 34 mole % of R-40 and about 2 mole % to about 25 mole % of R-134a.

2. The process for purification of R-1234yf feed as claimed in claim 1, further comprising the steps of:
   a) passing the feed to a distillation column to separate top composition of ternary azeotrope composition "A" comprising R-1234yf, R-40 and R-134a;
   b) optionally passing the ternary azeotrope composition "A" comprising R-1234yf, R-40 and R-134a through at least one member selected from the group consisting of an absorption tower, an adsorption tower and semipermeable membrane;
   c) passing the composition obtained from step b) to another distillation column to separate top composition of binary azeotrope composition "B" comprising R-1234yf and R-134a and bottom composition comprising substantially pure R-1234yf.

3. The process of claim 2, wherein the absorption tower contains chloroform or methanol.

4. The process of claim 2, wherein the adsorption tower contains molecular sieves having mean pore diameter of the size ranging from 3 Å to 5 Å.

5. The process of claim 2, wherein semipermeable membrane includes polyethene or polypropylene.

6. A process for purification of 2,3,3,3-tetrafluoro-1-propene (R-1234yf) feed comprising R-1234yf, chloromethane (R-40), 1,1,1,2-tetrafluoroethane (R-134a), 1,1,2,2-tetrafluoroethane (R-134), 1,1,3,3,3-pentafluoropropene (R-1225zc), and octafluorocyclobutane (OFCB), said process comprising a step of separating a binary azeotrope composition "B" comprising about 10 mole % to about 35 mole % of R-134a and about 65 mole % to about 90 mole % of R-1234yf.

7. The process for purification of R-1234yf feed as claimed in claim 6, said feed further comprising chlorodifluoromethane (R-22), said process further comprising the steps of:
a) passing the feed to a distillation column to separate top composition comprising R-22, OFCB, R-1234yf, R-40 and R-134a;
b) passing the top composition comprising R-22, OFCB, R-1234yf, R-40 and R-134a through at least one member selected from the group consisting of an absorption tower, adsorption tower and semipermeable membrane;
c) passing the composition obtained from step b) to another distillation column to separate top composition of binary azeotrope composition "B" comprising R-1234yf and R-134a and bottom composition comprising pure R-1234yf.

8. A process for purification of 2,3,3,3-tetrafluoro-1-propene (R-1234yf) feed comprising R-1234yf, chloromethane (R-40), 1,1,1,2-tetrafluoroethane (R-134a), 1,1,2,2-tetrafluoroethane (R-134), 1,1,3,3,3-pentafluoropropene (R-1225zc), and octafluorocyclobutane (OFCB), said process comprising a step of separating a ternary azeotrope composition "C" comprising about 70 mole % to about 85 mole % of R-1234yf, about 5 mole % to about 15 mole % of R-134 and about 2 mole % to about 20 mole % of R-134a.

9. The process for purification of R-1234yf feed as claimed in claim 8, further comprising a step of separating a binary azeotrope composition "D" comprising about 5 mole % to about 15 mole % of R-134 and about 85 mole % to about 95 mole % of R-1234yf.

10. The process for purification of R-1234yf feed as claimed in claim 8, further comprising the steps of:
a) passing the feed through a member selected from the group consisting of an absorption tower, adsorption tower and semipermeable membrane, to obtain a flowthrough;
b) passing the flowthrough obtained from step a) to a distillation column to separate top composition of ternary azeotrope composition "C" comprising R-1234yf, R-134, and R-134a and bottom composition comprising substantially pure R-1234yf;
c) recycling the top composition of ternary azeotrope.

* * * * *